(12) United States Patent
Navran, Jr. et al.

(10) Patent No.: US 6,902,909 B2
(45) Date of Patent: Jun. 7, 2005

(54) METHODS FOR EFFICIENT PRODUCTION OF MAMMALIAN RECOMBINANT PROTEINS

(75) Inventors: Stephen S. Navran, Jr., Houston, TX (US); Roger Akers, Houston, TX (US); William J. Anderson, Richmond, TX (US); Adrian F. Dinges, Jr., Houston, TX (US)

(73) Assignee: Synthecon, Inc., Houston, TX (US)

( * ) Notice: Subject to any disclaimer, the term of this patent is extended or adjusted under 35 U.S.C. 154(b) by 149 days.

(21) Appl. No.: 10/614,428

(22) Filed: Jul. 7, 2003

(65) Prior Publication Data

US 2004/0014177 A1 Jan. 22, 2004

Related U.S. Application Data

(60) Provisional application No. 60/394,597, filed on Jul. 9, 2002, and provisional application No. 60/430,795, filed on Dec. 4, 2002.

(51) Int. Cl.[7] ............................................. C12P 21/02
(52) U.S. Cl. ..................................................... 435/69.1
(58) Field of Search ......................................... 435/69.1

(56) References Cited

U.S. PATENT DOCUMENTS

| | | | | |
|---|---|---|---|---|
| 5,026,650 A | * | 6/1991 | Schwarz et al. | 435/297.1 |
| 5,256,411 A | * | 10/1993 | Bolton et al. | 424/139.1 |
| 5,637,477 A | * | 6/1997 | Spaulding et al. | 435/69.1 |
| 5,962,324 A | | 10/1999 | O'Connor et al. | 435/394 |
| 6,080,581 A | * | 6/2000 | Anderson et al. | 435/394 |
| 6,100,072 A | * | 8/2000 | Brucato et al. | 435/69.7 |
| 6,124,437 A | * | 9/2000 | Hirao et al. | 530/387.1 |
| 6,350,589 B1 | * | 2/2002 | Morris et al. | 435/41 |

OTHER PUBLICATIONS

Julkunen et al., "Complete amino acid sequence of human placental protein 14: A progesterone–regulated uterine protein homologous to beta–lactoglobulins," Proc. Natl. Acad. Sci, USA, vol. 85, pp. 8845–8849, Dec. 1988.*
Morrow et al., "Hematopoietic Placental Protein 14 An Immunosuppressive Factor in Cells of the Megakaryocytic Lineage," Am. J. Pathology, vol. 145, No. 6, Dec. 1994, pp. 1485–1495.*
Verma et al., "Antibody engineering: Comparison of bacterial, yeast, insect and mammalian expression systems," J. Immunologocal Methods, 216 (1998) pp. 1565–181.*
Rai et al., "Expression systems for production of heterologous proteins," Current Science (Bangalore), vol. 80, No. 9, May 10, 2001, pp 1121–1128.*
Alper, Joseph Searching for Medicine's Sweet Spot in Science 291:2338, 2001.
Bolton, A.E., Clough, K.J., Stoker, R.J., Pockley, A.G., Mowles, E.A., Westwood, O.M.R., and Chapman, M.G. Identification of placenta protein 14 as an immunosupressive factor in human reproduction. Lancet 1:593–595, 1987.
Cherry, R. and Papoutsakis, E.T., Physical Mechanisms of Cell Damage in Microcarrier Cell Culture Bioreactors. Biotechnolo. Bioeng. 32:1001–1004, 1988.
Cherry, R.S. and Hulte, C.T., Cell Death in the Thin Films of Bursting Bubbles. Biotechnol. Prog. 8:11–18, 1992.

(Continued)

Primary Examiner—Robert A. Wax
(74) Attorney, Agent, or Firm—Elizabeth R. Hall

(57) ABSTRACT

A process has been developed for the production of human recombinant polypeptides using transformed mammalian cells cultured in a horizontally rotating culture vessel modulated to create low shear, high mass transfer conditions. The resulting recombinant polypeptide has bioactivity and is produced in increase amounts.

23 Claims, 9 Drawing Sheets

OTHER PUBLICATIONS

Croughan, M. and Wang, D.I.C., Growth and death in overagitated microcarrier cell cultures. Biotechnol. Bioeng. 33:731–744, 1989.

Curling, E.M., Hayter, P.M., Baines, A.J., Bull, A.T., Gull, K., Strange, P.G., and Jenkins N. Recombinant human interferon–y. Differences in glycosylation and proteolytic processing lead to heterogeneity in batch culture. Biochem, J. 272:333–337. 1990.

Duray, P.H., Hatfill, S.J., and Pellis, N.R., Tissue Culture in Microgravity, Science & Medicine, May/Jun. 1997.

Furmanski, P., A pregnant possibility: Crossing fetal tolerance with hematopoiesis. Am. J. Pathol. 145:1485–1495, 1994.

Goodwin, T.J., Prewitt, T.L., Wolf, D.A. and Spaulding, G.F., Reduced Shear Stress: A Major Component in the Ability of Mammalian Tissues to Form Three–Dimensional Assemblies in Simulated Microgravity. J.Cell Biochem. 51:310–311, 1993.

James, D.C., Freeman, R.B., Hoare, M., Ogonah, O.W., Rooney, B.C., Larlonov, O.A., Dobrovolsky, V.N., Lagutin, O.V., Jenkins, N. N–Glycosylation of Recombinant Human Interferon–y Produced in Different Animal Expression Systems. Biotechnology 13:592–596, 1995.

Julkunen, M., Wahlstrom, T., Seppala, M., Koistinen, R., Koskimies, A., Stenmar, U.H., and Bohn, H., Detection and Localization of Placental Protein 14–Like Protein in Human Seminal Plasma and in the Male Genital Tract. Arch Androl. 12 (Suppl):59–67, 1984.

Kunas, K.T., and Papoutsakis, E.T. Damage mechanisms of suspended animal cells in agitated bioreactors with and without bubble entrainment. Biotechnol. Bioeng. 36:476–483, 1990.

Maeder, T., Sweet Medicines,Scientific American, p. 40–47, Jul. 2002.

Okamoto, N., Uchida, A., Kenji, T., Yoshitaka, K., Hideharu K., Rittinen, L., Koistinen, R., Seppälä, M., Mori, T. Suppression by human placental protein 14 of natural killer cell activity. Am. J. Reprod. Immunol. 26: 137–142, 1991.

Park, J.H., Lee, J.M. and Chung, I.S., Production of Recombinant Endostatin from Stably Transformed *Drasophila Melanogaster* S2 Cells. Biotechnology Lett. 21:729–733, 1999.

Petersen, J. F., McIntire, L. V., and Papoutsakis, E. T., Shear sensitivity of cultured hybridoma cells (CRL–8018) depends on mode of growth, culture age and metabolite concentration. J. Biotechnol. 7: 229–246, 1988.

Pockley, A.G. and Bolton, A.E. Placental protein 14 (PP14) inhibits the synthesis of interleukins–2 and the release of soluble interleukins 2 receptors from phytohemaglutinin–stimulatedlymphocytes. Clin. Exp. Immunol. 77: 252–256, 1989.

Pockley, A.G. and Bolton, A.E., The Effect of Human Placenta Protein 14 (PP14) on the Production of Interleukin 1 from Mitogenically Stimulated Mononuclear Cell Cultures. Immun. 69:277–281, 1990.

Pockley, A.G., Mowles, E.A., Stoker, R.J., Westwood, O.M.R., Chapman, M.G., and Bolton, A.E. Suppression of in vitro lymphocyte reactivity to phytohemaglutinin by placental protein 14. J. Reprod. Immunol. 13: 31–39, 1988.

Sambrook,J., Fritsch, E.F., and Maniatis, T. Molecular Cloning: A Laboratory Manual, 2nd Edition, Cold Spring Harbor Laboratory press, 1989.

Tsao, Y.D., Goodwin, T.J., Wolf, D.A., and Spaulding, G.F. Responses of Gravity Level Bariations on the NASA/JSC Bioreactor System. Proceedings of the 13th Annual Meeting of the IUPS Commission on Gravitational Physiology. San Antonio, Physiologist 35 (1 Suppl.): S49–S50, 1992.

Unsworth, B.R. and Lelkes, P.I., Growing tissues in microgravity. Nature Medicine 4(8): 901–907, 1998.

* cited by examiner

METHODS FOR EFFICIENT PRODUCTION OF MAMMALIAN RECOMBINANT PROTEINS

CROSS REFERENCE TO RELATED APPLICATIONS

This application claims priority to pending U.S. patent application Ser. No. 60/394,597 filed Jul. 9, 2002 by inventor Steve Navran and entitled "Methods for Efficient Production of Recombinant Proteins" and to pending U.S. patent application Ser. No. 60/430,795 filed Dec. 4, 2002 by inventors Roger Akers, William Anderson, Steve Navran and Adrian Dinges and entitled "Culture Vessels for Biologicals." The entire text of the above-referenced disclosures is incorporated by reference herein.

STATEMENT REGARDING FEDERALLY FUNDED RESEARCH

Research leading to this invention was federally supported, in part, by SBIR grant no. 95-1 15.04-2582 from the National Aeronautics and Space Administration, and the U.S. Government has certain rights thereunder in this invention.

BACKGROUND OF THE INVENTION

1. Field of the Invention

The present invention generally relates to a process for the production of human recombinant polypeptides using transformed mammalian cells. More particularly, the present invention relates to a process for producing enhanced quantities of biologically active recombinant protein using mammalian cells cultured in horizontally rotating culture vessels.

2. Description of the Related Art

In vitro cultures of animal cells are hosts for an increasing assortment of recombinant protein products. Recombinant proteins derived from animal cells are employed in a range of disciplines from agriculture to medicine to basic research. Progress made in genetic engineering and animal cell cultivation has enabled the production of an increasing assortment of recombinant proteins in sufficient quantities for the development of new drug therapies (e.g., plasminogen activator).

At present, both prokaryotes and eukaryotes are utilized as hosts for commercial production of recombinant proteins. The choice of one over the other is based on the structural complexity of the protein being produced, the desired yield and cost effectiveness. In cases where the native protein is not post-translationally modified, or where post-translational modification does not significantly affect protein function, the recombinant protein can be produced in prokaryotic organisms such as bacteria. Prokaryotes are preferred because their doubling times are in hours, rather than the days required for animal cell doubling. Likewise, prokaryotes yield grams of protein per liter of media, rather than the milligrams per liter produced in animal cells. Problems with the production of quantities of biologically active recombinant proteins for commercial use have encouraged investigators to use other types of cells, such as insect cells to try to increase the quantity of produced protein.

Yet there are many important human proteins that must undergo extensive post-translational processing and modification after syntheses of the amino acid chain itself (e.g., glycosylation, phosphorylation or macromolecular assembly) to be functional. Bacteria do not have the mechanisms for the correct post-translational modification of human proteins. While insect and non-human mammalian cells and transgenic animals can produce modifications similar to human cells, there are clear differences. For instance a recent study comparing glycosylation of recombinant human gamma interferon in Chinese hamster ovary ("CHO") cells, Sf9 insect cells and the mammary gland of transgenic mice showed that in each case, the patterns of glycosylation were distinctly different from that of the naturally occurring protein [James, D. C. et al. 1995]. Such differences can influence the secretion, biological activity, antigenicity and stability of the protein. For example, current techniques used to produce complex recombinant proteins such as Epogen, produced by Amgen, do not provide for the proper posttranslational modification of the protein. The degree of this problem is illustrated in an article in *Science* 291:2338, 2001 stating that Amgen had to discard 80% of its recombinant Epogen because of incorrect glycosylation.

Because animal cells are not enclosed in a cell wall like bacteria, they are susceptible to hydrodynamic forces within a bioreactor. Agitation, shear and other hydrodynamic phenomena have a profound effect on cell morphology and physiology, which can result in cell damage and death [Spaulding et al. 1997]. From a morphological perspective, hydrodynamic forces alter cell shape, adhesion, and membrane integrity, which can lead to cell death from lysis, detachment of anchorage-dependent cells from surfaces, and reduced metabolic activity [Croughan, M. et al. 1989 and Petersen, J. F. et al. 1988].

There are two main types of bioreactors that have been used in recombinant protein production in mammalian cells (i.e., the stirred tank and the perfused hollow fiber bioreactor). In perfused, hollow fiber bioreactors, cells are grown on one side of a semi-permeable membrane while the medium is perfused on the other side. Oxygen and nutrients can diffuse from the media compartment to the cell compartment. Metabolic wastes and secreted products can diffuse from the cell compartment to the media compartment. The advantages of this system include the lack of mechanical stress applied and the easy recovery of secreted proteins. However, the cells are grown on the surface of the fibers and the fibers limit cell growth to two dimensions. In addition, because the secreted proteins diffuse into the media compartment the secreted proteins are diluted in a large volume of media making downstream purification more difficult and expensive. Furthermore, the hollow fiber bioreactors are limited in size and are not practical to scale-up to large volumes.

The stirred-tank reactor is the system of choice for most companies because of its flexibility. These reactors can maintain cells in suspension with or without microcarriers by agitation through mechanical stirring with an impeller or gas bubble sparging. The stirred-tank reactors can be operated in different feed modes, and can be scaled up to very large volumes (e.g., 10,000 liters) These systems provide a large surface area for cell growth and the efficient transfer of nutrients, oxygen and metabolic wastes. The stirred-tank reactor maintains a homogenous environment throughout the reactor, and prevents cells from settling by a continuous stirring or mixing of the components within the reactor. But in the stirred-tank bioreactors, mixing can also cause cell damage from the resultant hydrodynamic forces attributed to bulk-fluid turbulence and gas/liquid interfaces [Kunas, K. T. et al. 1990]. Typically, these interfaces arise during cultivation as a result of sparging, vortex formation, turbulent eddies, fluid-wall shear gradients and surface oxygenation. Thus, a major disadvantage of the stirred-tank reactor is that shear stress causes significant cell injury and death, leading to lower levels of recombinant protein production, or lower yield.

In each of these conventional bioreactors, some recombinant proteins cannot be produced in sufficient quantities or a high enough specific activity to allow the proteins to be used for commercial purposes. This is particularly a problem in the production of human proteins of medical interest. It is speculated that the production of such proteins in human cells could provide a protein with greater specific activity, or higher bioreactivity, thereby reducing the quantity of protein needed to give a therapeutic result.

There is a continuing need to improve mammalian, particularly human, cell culture techniques to achieve commercial scale recombinant protein production. In addition, there is a continuing need to develop techniques providing appropriately post-translationally modified proteins having sufficient bioactivity for therapeutic purposes. Furthermore, a need exists for a means of producing the recombinant protein in a high enough concentration to ease the time and expense of subsequently purifying the protein.

SUMMARY OF THE INVENTION

The present invention is a method for efficient, high yield production of recombinant proteins that are post-translationally modified. This method includes the use of a micro-gravity, rotating bioreactor to produce a recombinant protein of a class that requires complex post-translational processing in human cells in order to exhibit its full biological activity, stability, and/or lack of immunogenicity in vivo.

One aspect of the present invention includes identifying and cloning a therapeutic polypeptide that is post-translationally modified; identifying a cell line from a tissue type that normally produces the polypeptide; transfection of the cell line with a recombinant expression plasmid carrying the transgene for the polypeptide; expansion of the transfected cells in a horizontally rotating bioreactor; and collection of the recombinant polypeptide.

Another aspect of the present invention is a method for production of a human proteinaceous therapeutic molecule including the steps of: (a) identify a mammalian cell line derived from a tissue that produces the proteinaceous therapeutic molecule in nature; (b) transfecting a plurality of cells from the mammalian cell line with a gene coding for the human proteinaceous therapeutic molecule; (c) cloning the transfected cells expressing the human proteinaceous therapeutic molecule; (d) expanding the cloned cells in a rotating cell culture system filled with a culture media, wherein the rotating cell culture system provides a simulated micro-gravity environment for the expanding cloned cells; (e) separating a volume of culture media from the expanded cloned cells; and (f) isolating a protein fraction from the volume of culture media, wherein the protein fraction is rich in the proteinaceous therapeutic molecule.

Yet another aspect of the present invention is a method for the production of recombinant human proteins comprising: (a) selecting a post-translationally modified human protein; (b) identifying a human cell line derived from a tissue that produces the human protein; (c) transfecting a plurality of cells from the human cell line with a gene coding for the human protein and a bioselection mechanism; (d) cloning the transfected cells expressing the human protein and the bioselection mechanism; (e) introducing the cloned transfected cells into a rotating cell culture system filled with a culture media; and (f) growing the cloned transfected cells in the rotating cell culture system, wherein the cloned cells synthesize the human protein and excrete the human protein into the culture media in the rotating cell culture system.

Still yet another aspect of the present invention is a method for the production of recombinant human proteins comprising: (a) selecting a post-translationally modified human protein; (b) identifying a human cell line derived from a tissue that produces the human protein; (c) transfecting a plurality of cells from the human cell line with a gene coding for the human protein and a bioselection mechanism; (d) cloning the transfected cells expressing the human protein and the bioselection mechanism; (e) providing a horizontally rotating cell culture system having a molecular weight cut-off membrane transversing a growth chamber of the cell culture system, wherein the rotating cell culture system provides a low shear environment less than or equal to 2 dynes/cm$^2$;

(f) introducing the cloned transfected cells into the growth chamber of the rotating cell culture system filled with a culture media; (g) maintaining a flow of the culture media through the growth chamber of the rotating cell culture system; (h) expanding the cloned transfected cells in the rotating cell culture system, wherein the cloned cells synthesize the human protein and excrete the human protein into the culture media in the rotating cell culture system; (i) separating the cloned transfected cells from a volume of the culture media containing the excreted human protein; and (j) isolating a protein fraction from the volume of the culture media, wherein the protein fraction is rich in the human protein.

The foregoing has outlined several aspects of the present invention in order that the detailed description of the invention that follows may be better understood. Additional features and advantages of the invention will be described hereinafter which form the subject of the claims of the invention. It should be appreciated by those skilled in the art that the conception and the specific embodiments disclosed might be readily utilized as a basis for modifying or redesigning the method or process for carrying out the same purposes as the invention. It should be realized that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DESCRIPTION OF THE ILLUSTRATIVE EMBODIMENTS

Figure 1:
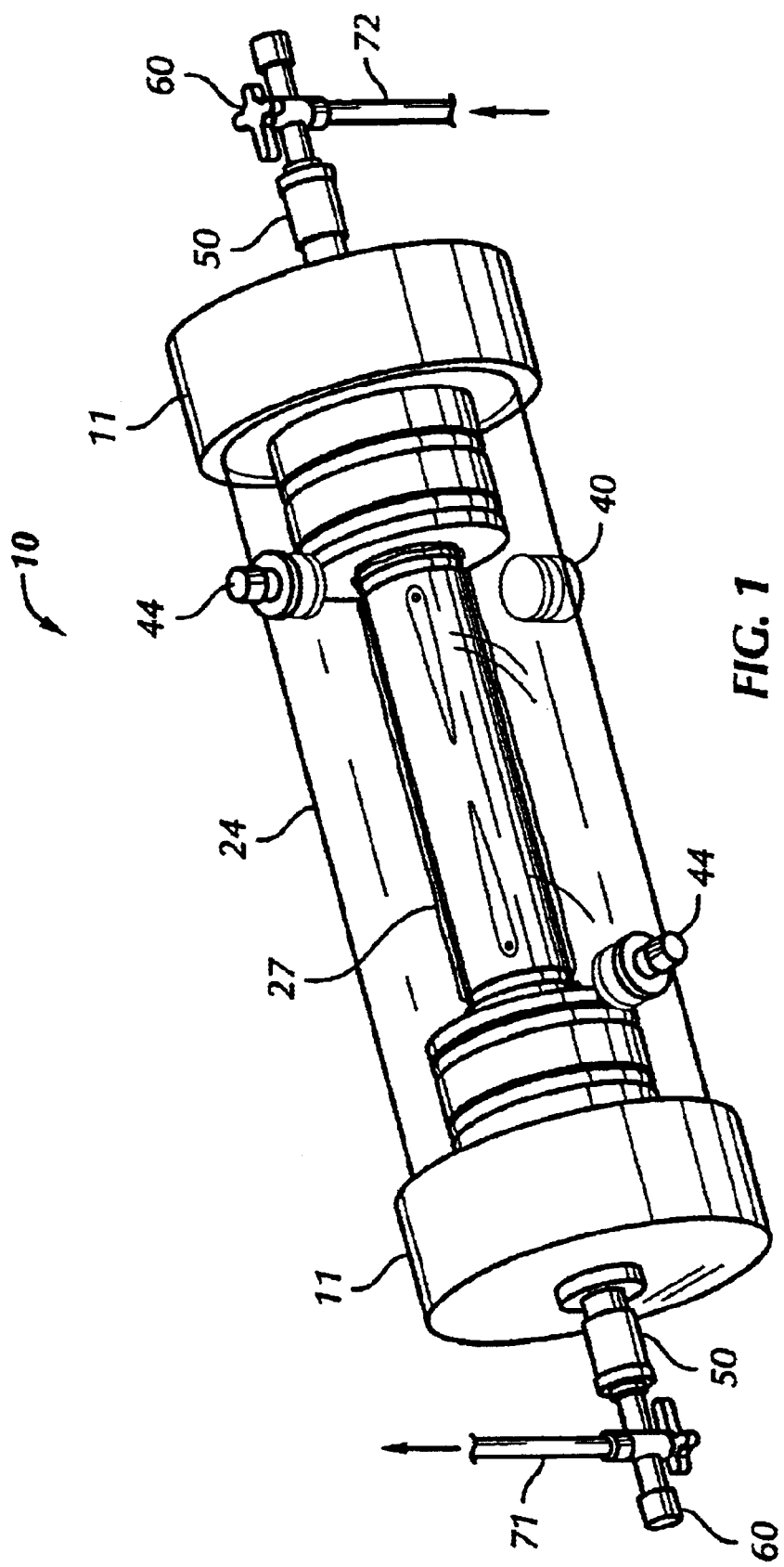
FIG. 1 shows an oblique view of a rotating cell culture chamber having a molecular weight cut-off membrane.

To address the need for increased quantities of biologically active proteinaceous therapeutics the present invention cultures transfected mammalian cells is a low shear, high mass transfer cell culture system under conditions that produce recombinant proteins in higher yields.

I. Cell Culture System

Cell viability has been shown to decrease at shear stresses of 5–7 dynes/cm$^2$ [Cherry, R. et al. 1988]. Thus, the present invention utilizes a low shear cell culture system of about 2 dyne/cm$^2$ and preferably about 1 dyne/cm$^2$. For example, conventional stirred bioreactors traumatize cells with over-agitation [Croughan, M. et al. 1989]. Furthermore, stirred bioreactors rely on oxygenation at the gas-liquid interface or sparging where the gas is introduced into the fluid as small bubbles, creating cell membrane damaging turbulence [Cherry, R. S. et al 1992]. The cell culture system of the present invention avoids this problem by oxygenating the media through an external gas exchange membrane in the flow loop, permitting gas to diffuse without creating bubbles, thereby reducing cell damage and enhancing cell growth.

This gentle environment allows the cells to expend more of their metabolic energy on growth and other normal processes rather than repairing injury. These conditions have been shown to promote the formation of high density, stable, tissue-like structures from primary cell isolates or immortalized cell lines [Unsworth, B. R. et al. 1998; Goodwin, T. J. et al. 1993; and O'Connor et al. U.S. Pat. No. 5,962,324]. However, three dimensional tissues are not considered suitable for commercial recombinant protein formation as there is concern about the appropriate oxygen and nutrient delivery to the interior cells and the ability to sufficiently remove cellular waste.

To reduce the formation of three dimensional multi-cellular tissues, stably transfected *Drosophila melanogaster* S2 cells have been used to produce recombinant endostatin in a low shear stress rotating cell culture system ("RCCS") [Park, J. H. et al. 1999]. But insect cells are distinctly different from animal cells and the use of these cells does not solve the problems described by investigators in dealing with human cell cultures [Spaulding et al. U.S. Pat. No. 5,637,477]. Furthermore, although insect cell lines perform a number of key post-translational modifications, the modifications are not identical to those in human cells and can reduce the specific activity of the protein produced. Specific activity is herein defined as the biological activity per given amount of protein (i.e., Units of activity/mg protein).

The present invention uses low shear stress (less than 2 dyne/cm$^2$) and high mass transfer cell culture techniques, to produce recombinant proteins that undergo complex post-translational modification in transfected human cells, or other suitable mammalian cells, on a large scale in an efficient manner that results in a high yield of biologically active recombinant protein.

EXAMPLE 1

Rotating Cell Culture System ("RCCS")

One embodiment of the cell culture system used in the present invention is a bioreactor, such as the RCCS developed at the National Aeronautics and Space Administration, that incorporates a horizontally rotating, zero head space cylindrical vessel that simulates micro-gravity by randomizing the gravitational forces experienced by the cells suspended in the vessel as described in U.S. Pat. No. 5,026,650 issued to Schwartz, et al. Improvements to the culture vessel of U.S. Pat. No. 5,026,650 are described in U.S. Pat. No. 6,080,581 issued to Anderson, et al. The entire text of U.S. Pat. Nos. 5,026,650 and 6,080,581 are incorporated by reference herein. This embodiment of the RCCS will be referred to herein as the batch rotating cell culture system or the RCCS-MG.

The formation of three dimensional multi-cellular aggregates is controlled in this cell culture system by growing anchorage-dependent cells on microcarriers and maintaining non-adherent cells in suspension. The simulated micro-gravity environment of this RCCS avoids the turbulence and shear stresses that cause injury to cells cultured in conventional stirred bioreactors. Cells grown in this RCCS are subjected to shear stresses of only about 0.8 dynes/cm$^2$ [Physiologist 35(1Suppl):S49–S58, 1992].

EXAMPLE 2

A Rotating Cell Culture System ("RCCS") Transversed by a Molecular Weight Cut-Off Membrane Alternatively, the present invention may utilize either the reusable or the disposable culture vessel described in pending U.S. patent application Ser. No. 60/430,795, the entire text of which is incorporated herein by reference. This RCCS has a horizontally rotating, zero head space cylindrical vessel that provides a low shear stress, high mass transfer environment for cultured cells as well as a molecular weight cut-off membrane transversing the growth chamber. This embodiment of the RCCS will be referred to herein as the perfused rotating cell culture system or the RCCS-MWM culture system.

This culture vessel is easily scaled-up to large volumes (e.g., 1,000 liters) by having multiple membranes transversing the culture compartment to ensure that fluid entering through the inlet means of the culture chamber perfuses throughout the interior of the culture compartment and is well mixed with the media within the culture compartment.

Figure 2:
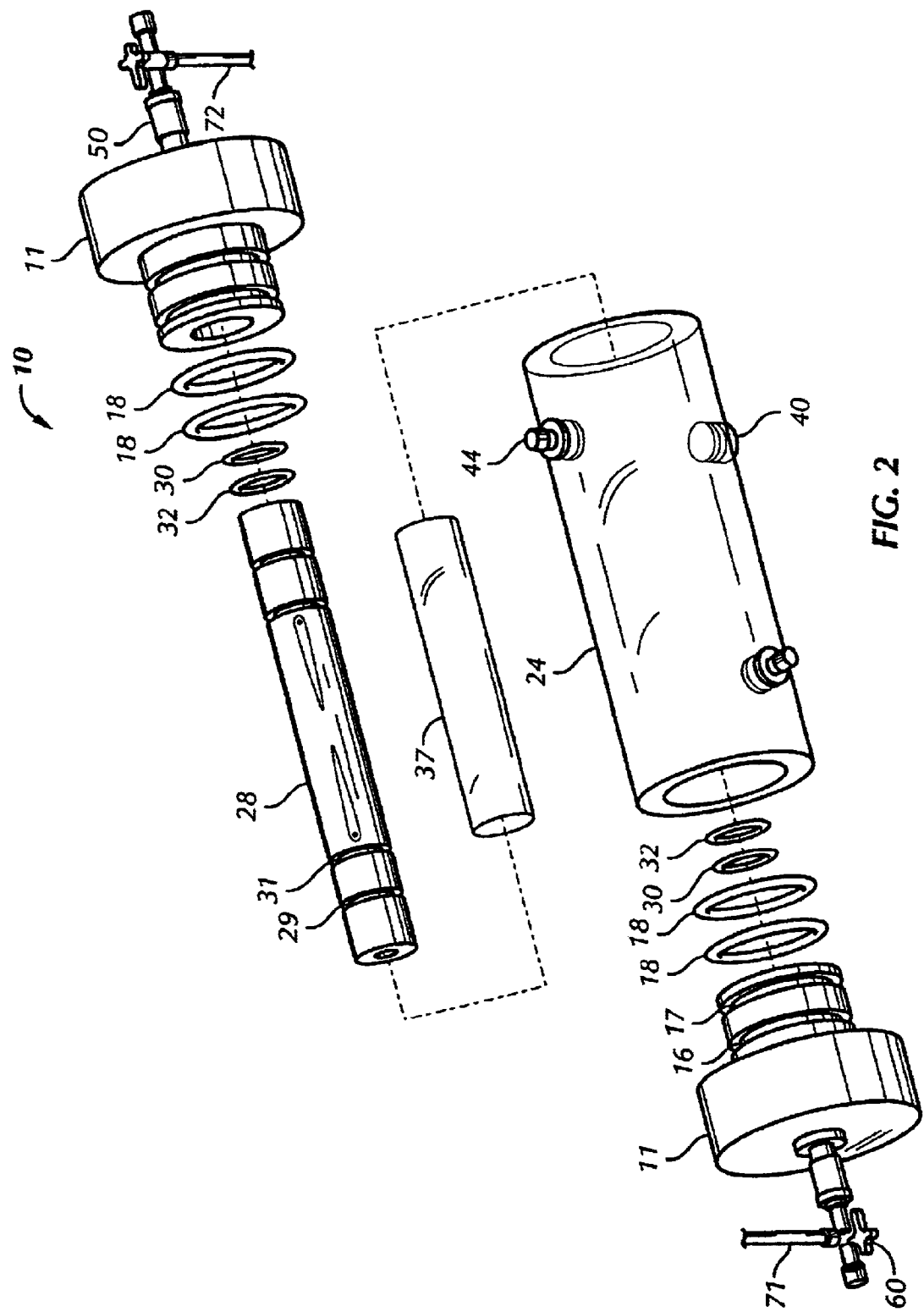
FIG. 2 shows an exploded oblique view of the cell culture chamber of FIG. 1.
Figure 3:
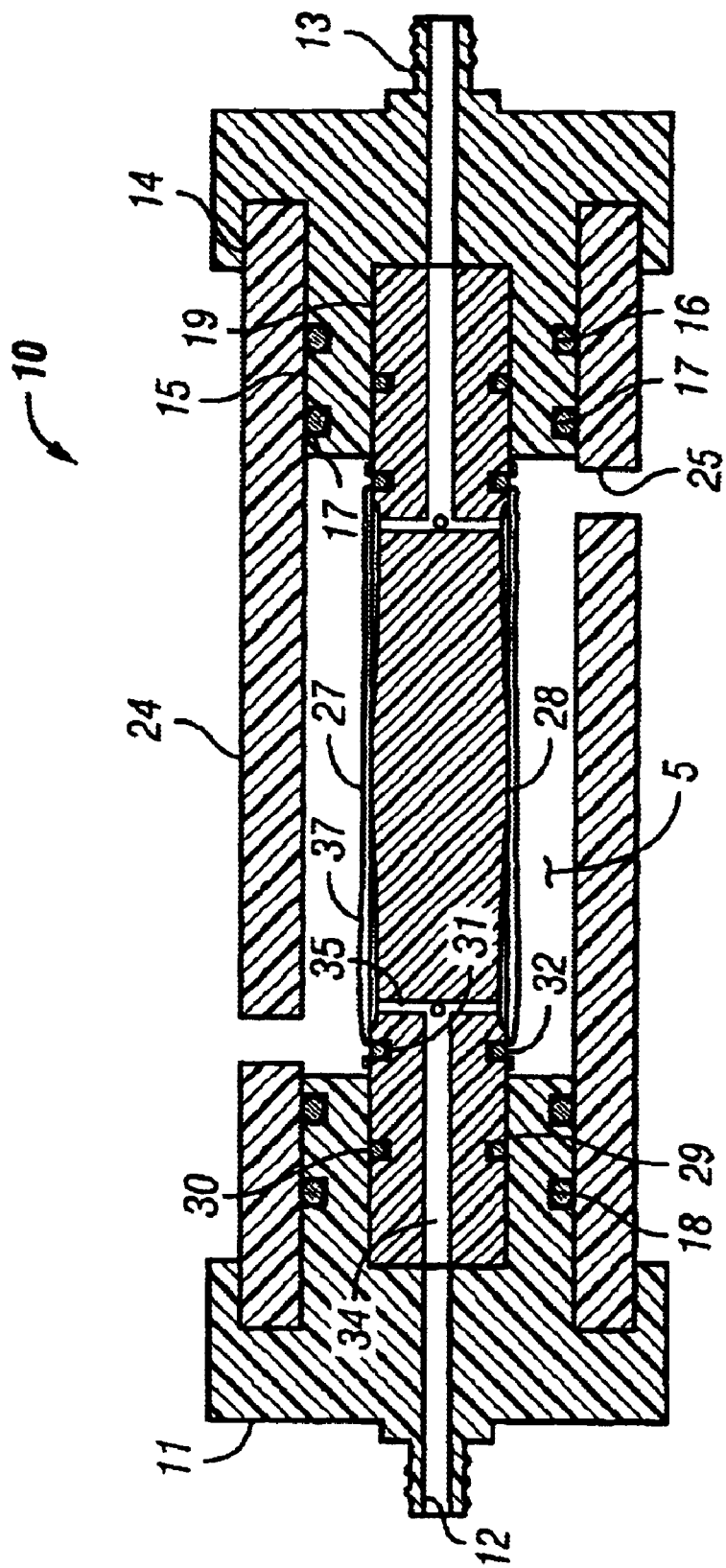
FIG. 3 is shows a longitudinal cross-sectional view of the cell culture chamber of FIG. 1 with the end swivels and shutoff valves removed.

One embodiment of the RCCS-MWM is culture chamber 10 illustrated in FIGS. 1–3. The culture chamber 10 has a molecular weight cut-off membrane that transverses the culture compartment to permit two-way perfusion into and out of the cell growth chamber. FIG. 1 shows one embodiment of a reusable culture chamber 10. As shown in FIGS. 1–3, two identical end pieces 11 seal the ends of right circular cylindrical tubular sleeve 24 so that a growth compartment 5 is formed within the enclosed space. The culture chamber is designed to be supported on and rotated by a roller drive that rotates the chamber about its axis. A variety of drive assemblies may be used to rotate the culture chamber such as the drive assembly described in U.S. Pat. No. 6,080,581 issued on Jun. 27, 2000 to Anderson and Dodd. The entire specification of U.S. Pat. No. 6,080,581 is hereby incorporated by reference.

The biologicals being cultured in the rotatable chamber require nutrients, so fluid-conducting swivels 50, stopcock valves 60, and fluid inlet tubing 72 and outlet tubing 71 are provided on the ends of the housing 10 so that the entry and exit of media is controlled. Multiple radial wall penetration ports 25 are provided in the annular wall of sleeve 24 to allow the introduction of one or more fill ports 40 and one or more vent ports 44.

The particulars of the construction of the components of culture chamber 10 are shown in FIGS. 1–5. End piece 11 has a right circular cylindrical central body having a coaxial attachment neck 13 on its outer face. Axial through hole 12 penetrates through the 13 attachment neck and the rest of the body of end piece 11. Reduced diameter coaxial right circular cylindrical interior projection 15 extends inwardly on the transverse face of the interior end of end piece 11, with a flat-bottomed trepanned groove 14 located on the transverse interior face of end piece 11 immediately exterior of projection 15. The exterior cylindrical surface of interior projection 15 has, in order from the interior transverse face of end piece 11, first and second annular male O-ring grooves 16 and 17. Elastomeric O-rings 18 are mounted in O-ring grooves 16 and 17. At the interior end of interior projection 15 of end piece 11, flat-bottomed coaxial counterbore 19 intersects through hole 12. An optional lead-in chamfer may be provided at the mouth of counterbore 19 in order to facilitate the stabbing of an O-ring seal with the membrane carrier assembly.

The right circular cylindrical sleeve 24 can be made of a variety of materials such as glass, stainless steel or plastic. Preferably the reusable cell culture chamber is constructed of plastic, typically a transparent plastic such as an acrylic plastic for the cylindrical sleeve 24 and opaque plastics such as Kynar™ or Delrin™ for the other rigid pieces such as the end pieces 11. Suitable plastics have substantially zero porosity and are substantially impermeable to gases and non-reactive to biological media and its components. Preferably the construction materials used are able to undergo multiple sterilizations by steam, gas, or radiation without deforming, cracking or otherwise being rendered unusable.

Although not shown in FIG. 3, the right circular cylindrical sleeve 24 is preferably provided with a lead-in taper on each of its interior corners to facilitate the stabbing of O-rings. The interior bore of sleeve 24 is a close sliding fit to the outer diameter of interior projection 15 of end fitting 11, thereby permitting O-rings 18 in the O-ring grooves 16 and 17 to sealingly engage the bore of sleeve 24. As stated previously, the sleeve 24 has multiple radial wall penetration ports 25 to allow the mounting of fittings used for inserting fluid into or removing fluids from the growth compartment 5 and for allowing gas to escape from the growth compartment 5 as it is being filled with fluid. At each end of chamber 10, sleeve 24 is stabbed over interior projection 15 and bottomed out in the trepanned groove 14 of an end piece 11.

The growth compartment 5 is located between the interior bore of the sleeve 24, the membrane carrier assembly 27, and the interior ends of the interior projection 15 of the end pieces 11. The growth compartment 5 is transversed by a membrane carrier assembly 27 as shown in FIGS. 1 and 3. An end of the generally cylindrical membrane carrier assembly 27 is mounted in the counterbore 19 of each of the two end assemblies 11 used in chamber 10.

Figure 4:
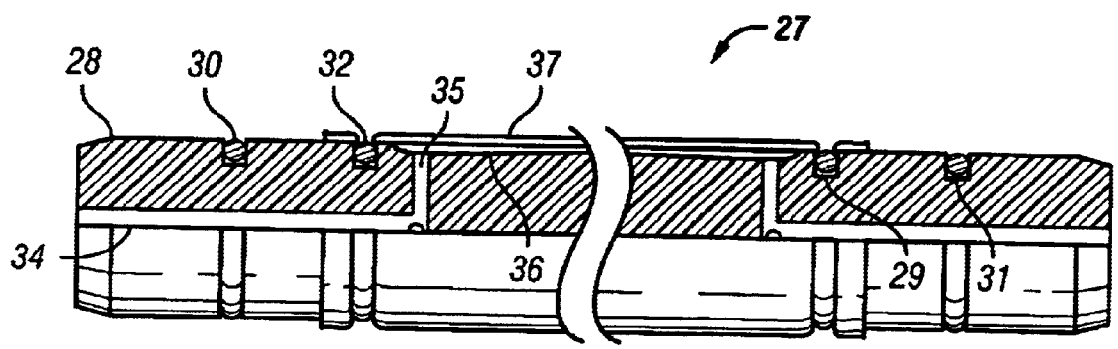
FIG. 4 is a longitudinal quarter-section of the membrane carrier assembly used in FIG. 1.

FIG. 4 shows the details of construction of membrane carrier assembly 27. Support cylinder 28 is symmetrical about its transverse midplane. The exterior of each end of cylinder 28 has, sequentially from its end, a lead-in taper to ease blind stabbing into a mounting hole, a first annular male O-ring groove 31 mounting elastomeric O-ring 30, and a second groove 29 configured similarly to an O-ring groove. Each end of cylinder 28 also has an axial blind hole 34 with multiple (in this case, four) equispaced coplanar radial cross holes 35 intersecting the inner end of blind hole 34. A small recessed surface pocket 36, having an arcuate cross-section, is located on the exterior of cylinder 28 and is intercepted by each radial cross hole 35. The depth of surface pockets 36 below the outside cylindrical diameter is largest near the intersection with its cross hole 35 and linearly tapers to zero towards the middle of cylinder 28.

Centrally deployed with a close fit around the exterior of cylinder 28 is a tubular molecular weight cut-off membrane 37. Membrane 37 is flexible with a limited amount of elastic stretch capability. The construction of membrane 37 is very carefully controlled so the number of molecules, having a molecular weight in excess of the specific limiting molecular weight cut-off value of the membrane 37, that transfuse through the membrane in either direction is statistically very small and rapidly decreases as a function of increasing molecular weight. Thus, there is essentially no passage of molecules, substantially larger than the molecular weight cut-off value of the membrane, through the membrane 37. The molecular weight cut-off value of the membrane 37 is preselected so that nutrients and growth factors, as well as metabolic waste products, can easily transfuse through the membrane, whereas larger cellular products can be retained. For example, Factor VIII (having a molecular weight of about 350,000 Daltons) or IgG monoclonal antibodies (having a molecular weight of about 155,000 Daltons) produced by genetically engineered bacteria or cells can be retained by a membrane with a molecular weight cut-off value of about 100,000 Daltons; whereas the majority of serum albumin (having a molecular weight of about 67,500 Daltons and making up 55% to 62% of serum protein) would be allowed to pass through the membrane.

Currently bioreactors and culture chambers are designed to have a filter to keep the cells within the chamber and to allow the desired therapeutic protein to pass out of the chamber with the waste products. The present invention allows the user to select a membrane having a molecular weight cut-off value that would permit the desired protein to pass out of the culture chamber with the waste products. However, the present invention also permits the user to select a membrane having a smaller molecular weight cut-off value than the desired protein, so that the desired protein is retained and accumulated within the culture chamber. The membrane carrier assembly 27 can be assembled with membranes 37 having a variety of molecular weight cut-off values, thereby allowing the user to select a molecular weight cut-off value appropriate for the protein production protocol.

Furthermore, the membrane carrier assembly 27 of the present invention provides a media circulating system that allows the user to constantly monitor certain media parameters in the culture chamber (e.g., the pH) and to adjust those parameters by adjusting the media being pumped into the culture chamber, thereby maintaining optimum conditions for the cells being cultured.

Figure 5:
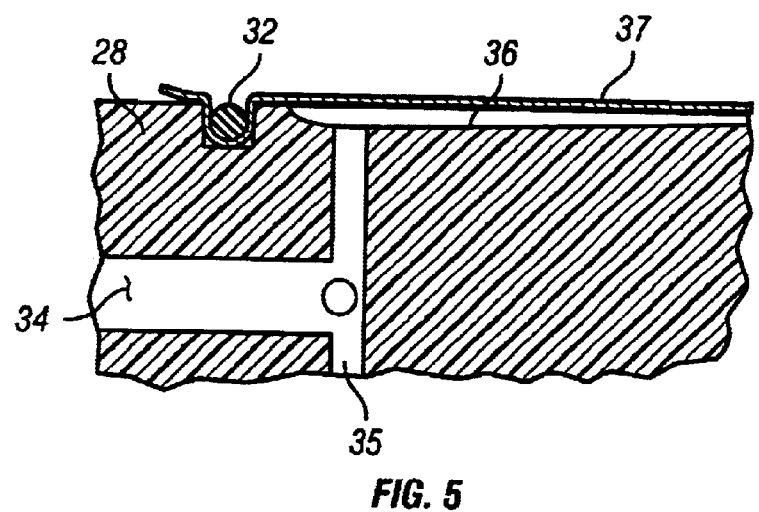
FIG. 5 is a partial longitudinal quarter-section of the membrane assembled on one end of the membrane carrier assembly used in FIG. 4.

As shown in FIG. 5, membrane 37 is sealed to the exterior of cylinder 28 by using O-ring 32 to circumferentially constrict over the exterior of membrane 37, thereby forcing it into sealing engagement with groove 31 on the outside of cylinder 28. In this manner, a small chamber in fluid connection with the radial flow passage 35 is formed between the exterior of surface pockets 36 and the interior of membrane 37. The depth and length of cut for the surface pockets 36 is predetermined to be sufficient to produce a sufficient pressure area so that the elastic resistance of membrane 37 can be overcome. The expansion of the membrane 37 when media is passed through flow passage 35 and along pockets 36 permits a thin flow sheet of media between the membrane 37 and cylinder 28 to be established.

Use of the culture vessel 10 and an appropriate molecular weight cut-off membrane 37 will allow nutrients, growth factors and gases in the input fluid entering through the inlet means of the culture chamber to perfuse into and throughout the interior of the culture compartment, while waste products perfuse out of the chamber through the molecular weight cut-off membrane in the reverse direction into the exiting fluid that passes through the interior of the membrane. Whenever the desired therapeutic product is relatively large, the molecular weight cut-off of the membrane 37 can be selected to prevent the desired recombinant therapeutic product from leaving the growth compartment. Under those circumstances, the recombinant therapeutic product will be concentrated in the growth compartment 5 making the subsequent purification and concentration of the product much easier.

II. Proteinateous Therapeutics

A preferred embodiment of the invention includes the identification and cloning of a human gene, which codes for a polypeptide or protein of therapeutic interest. Although all proteins are by definition polypeptides, not all polypeptides are considered to be proteins. In the context of this invention the terms "polypeptide" and "protein" will be used interchangeably.

The selected protein of the present invention will be of a class that requires complex post-translational modification in order to exhibit its full biological activity, stability, and/or lack of immunogenicity in vivo. In the context of the present invention, "post-translational processing" or "post-translational modification" of a protein includes any difference between a functional protein and the linear polypeptide sequence encoded between the initiation and termination codons of the polypeptide's structural gene. Post-translational modifications will include, but not be limited to, glycosylation, phosphorylation, disulfide linkages, modification of amino acid residues, or macromolecular assembly such as folding.

For example, glycosylation is one of the most extensive of all post-translational modifications that occur with native proteins. Glycosylation occurs in the endoplasmic reticulum and Golgi compartments of the cell and involves a complex series of reactions catalyzed by membrane-bound glycosyltransferases and glycosidases. Many of these enzymes are sensitive to other events that take place within a cell. Therefore, the population of carbohydrates that is then attached to an individual protein will depend on the cell type in which the glycoprotein is expressed as well as the physiological status of the cell. Therefore, the culture conditions and the types of cells used to produce recombinant glycoproteins are critical to the quality as well as the quantity of the final product.

PP14 is an example of a protein that fits the protein profile for the present invention in that it requires post-translational modification in human cells for full biological activity. PP14 is a 28 kiloDalton (kDa) protein that was originally isolated from placental tissues and was later found to be secreted from epithelial cells of the endometrium. This protein is markedly elevated during pregnancy and its expression pattern has been associated with protection of the fetus from immunological attack by the mother [Bolton et al. 1987]. The recent discovery of this protein in seminal fluid has indicated that PP14 also plays a role in protecting sperm from immunological attack in the female reproductive system [Julkunen, M. et al 1984]. Thus, placenta protein 14 has been identified as an immunosupressive factor in human reproduction. PP14 has also been shown to inhibit a number of immune system functions in vitro such as: reducing lymphocyte proliferation [Pockley, A. G. et al 1988], inhibiting mixed lymphocyte reactions [Bolton, A. E. et al 1987], decreasing the secretion of IL-2 and soluble IL-2 receptor [Pockley, A. G. et al. 1989], reducing IL-1 secretion from stimulated mononuclear cells [Pockley, A. G. et al. 1990], and inhibiting natural killer cell activity [Okamoto, N. et al. 1991].

PP14 is preferably produced in human cell lines in order to produce an optimally active glycosylated product with stable intra-molecular disulfide bonds. Therefore, this protein was selected to exemplify production according to the present invention due to its preference for human cell system expression, its lack of host toxicity, and its important role in a variety of physiological reactions, including its potential clinical use in organ transplantation.

Numerous other proteins exhibit similar characteristics (i.e., complex post-translational modification and known clinical applications). For example, human thrombopoietin (TPO) is well suited for production in the RCCS. Thrombopoietin is a primary regulatory factor in the production of platelets. The majority of human TPO is produced in hepatocytes and a lesser amount is produced in renal cells. Human TPO contains 332 amino acids with two internal disulfide bonds and 6 N-linked glycosylation sites. The glycosylated protein shows an apparent molecular weight of 82 kDaltons. The clinical application of TPO is for treatment of thrombocytopenias, especially those caused by chemotherapy or radiation therapy.

III. Selection and Culturing of Cell Lines

The choice of cell line used for the production of therapeutic proteins is important as it influences the post-translational processing of the protein coded by the transgene. In one embodiment the cell line chosen is derived from the same tissue type that normally expresses the protein. This does not guarantee that the post-translational processing of the selected protein will be identical to that of the native protein since the transfection event required to produce stable cell lines may result in altered processing. Biochemical and bioassay analysis will be used to determine recombinant protein activity and stability and to verify the choice of cell line.

Virtually any cell type can be cultured in the RCCS. Current practice in the commercial production of recombinant proteins is to produce them in a few well known cell lines, usually of rodent origin, that have been adapted to grow in spinner flasks under typical culture conditions. While this may allow for the production of some human proteins that approximate the normal biological activity of the native protein, many other therapeutically useful proteins will have to be produced in human cells and possibly even in particular types of human cells in order to achieve sufficient specific activity for therapeutic purposes.

The RCCS creates a low shear, high mass transfer environment which when optimized for a particular cell line allows even the most fastidious cell lines to be grown without requiring that the cells undergo extensive adaptation. A number of parameters which can potentially affect the quality and quantity of the protein produced can be optimized in the RCCS.

For example, control of the rotational speed of the RCCS is important in maintaining the cells in suspension while minimizing fluid shear stress on the cells. In the case of non-adherent cells, a speed of about 10 rpm is generally optimal, although small differences (depending on the cell line) have been observed. For anchorage-dependent cells, microcarriers must be used to prevent aggregation and three dimensional growth. As the cells become confluent on the microcarriers, the microcarriers may aggregate and produce larger, denser particles which sediment more rapidly. Accordingly, the rotational speed will be increased to offset the increased sedimentation rate. Typically, the rotational speed is increased to approximately 15–20 rpm to prevent sedimentation.

Media composition will also be optimized. By adding specialized sensors in the media flow loop, it becomes possible to continuously monitor the conditions within the bioreactor vessel, including pH, $O_2$, $CO_2$ and glucose. These parameters are fed into a computer, which then controls the flow rate of the media and will inject the appropriate solutions to maintain the media within pre-set parameters. For example, media glucose concentration can influence the degree of protein glycosylation. This was shown in a study that related the degree of glycosylation of interferon-γ to the ambient glucose concentration [Curling, E. M. et al. 1990]. While optimal media composition will vary with the cell line and recombinant protein to be produced, the continuous monitoring of media composition makes it relatively easy to maintain consistent levels of nutrients such as glucose.

EXAMPLE 3

Selection of K-562 Cells for the Production of PP14

The human myelogenous leukemia cell line, K-562, has been shown to produce PP14 endogenously when stimulated by activators of protein kinase C [Furmanski, P. 1994]. K-562 cells were selected as a candidate cell line for the production of PP14. K-562 cells were obtained from the American Type Culture Collection (ATCC #CCL-243).
IV. Cloning the Gene of Interest The cloning of the desired gene can be accomplished by a variety of methods well-known in the art of biotechnology either by screening a cDNA library made from a tissue known to express the gene of interest or by RT-PCR (reverse-transcriptase-polymerase chain reaction).

In the case of RT-PCR, the mRNA is isolated from cells or tissues, which express the gene of interest. The mRNA is converted to cDNA by reverse transcriptase and the specific gene is amplified by PCR using gene-specific primers. It is important that the complete cDNA be obtained including the 3' and 5' untranslated regions, since these sequences may have functions that enhance the expression of the gene. It is also important that the thermostable DNA polymerase used in the PCR reaction be a high fidelity enzyme with 3'-5' exonuclease proof reading activity to minimize the production of mutations which could alter biological activity.

If a cDNA library is used, it is screened using gene-specific primers and then amplified. This procedure avoids the need to use a cloning vector and then subclone into an expression vector.

After the cDNA has been obtained, it is cloned into an expression vector. The minimal requirements of the vector are that it has a constitutive promoter for high-level expression of the transgene and a selectable mark such as a neomycin resistance gene for selection of vector-containing clones. Other features may be included in the vector as needed such as affinity tags to assist in purification. If the protein is secreted, the signal sequence should be contained within the full length gene. Such methods are routine in the art. When the gene of interest has been ligated into the appropriate shuttle expression vector, it is amplified in *E. coli* and sufficient plasmid prepared for transfection directly into the selected cell line.

EXAMPLE 4

Cloning the PP14 Gene

The PP14 gene [Genebank Accession # NM002571] has been cloned and sequenced and inserted into a mammalian expression vector for transfection into K-562 cells pursuant to methods known in the art [Julkunen, M. et al. 1988].

The PP14 mRNA expression was induced in K-562 cells by treating them for 48 hours with 10 mM phorbol myristate acetate (PMA). The induced cells were harvested by centrifugation and the mRNA extracted using a Fast Track™ mRNA Isolation Kit (Invitrogen Corporation, Carlsbad, Calif.) according to the manufacturer's instructions. The cDNA was obtained using RT-PCR.

The first strand of cDNA was obtained by from the isolated mRNA by priming the mRNA with oligo(dT) and using MMLV reverse transcriptase. The cDNA was then synthesized by RT-PCR using the forward and reverse PP14-specific primers respectively set out below.

```
5'-AGGGAGCAGCCTCCCCTGGCAAT      [SEQ ID NO: 1]

5'-CATCCCTCTGGCTCCAGAGCTCAGA    [SEQ ID NO: 2]
```

The PCR was performed using a high fidelity, proofreading DNA polymerase Advantage™-HF2 from Clontech, Palo Alto, Calif. The cycles were run at 94° C. for thirty seconds followed by 68° C. for 3 minutes. The PCR product contained the entire 5' untranslated region and part of the 3'-untranslated region and was 763 base pairs in length as confirmed by agarose gel electrophoresis on a 1.5% TAE gel.

The resulting cDNA was then ligated into pCR-Blunt II-TOPO (Invitrogen Corporation, Carlsbad, Calif.) according to the manufacturer's instructions and transformed into *E. coli*. Since the cDNA was blunt ended, several clones were selected and sequenced in order to select clones with the correct orientation.

Properly oriented clones were then subcloned into an expression vector. An alternative forward PCR primer was designed to prime just inside the stop codon to allow PP14 to be produced as a fusion protein. The PCR was performed on the full length cDNA to produce a truncated cDNA that was ligated into the pCR-Blunt vector as described above. A correctly oriented clone was selected and treated with restriction enzymes, Hind III and Xho I to create the ends necessary to ligate in frame into the expression vector pcDNA6/myc-HIS (Invitrogen Corporation, Carlsbad, Calif.), to add a polyhistidine fusion tag to PP14. The plasmid containing the fusion gene was propagated in *E. coli* and a small preparation of the cDNA was produced.

V. Transfection of Cells

To produce commercial quantities of the selected polypeptide, recombinant expression vectors are introduced into the selected cell in which the recombinant polypeptide or protein is then expressed. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. The host cell of the present invention will be a mammalian cell and preferably a human cell.

Vector DNA can be introduced into the cells via conventional transfection techniques. As used herein, the term "transfection" is intended to refer to a variety of art-recognized techniques for introducing foreign nucleic acid (e.g., DNA) into a host cell, including, but not limited to, calcium phosphate or calcium chloride co-precipitation, DEAE-dextran-mediated transfection, lipofection, or electroporation. Suitable methods for transfecting host cells can be found in Sambrook et al., Molecular Cloning: A Laboratory Manual, 2nd Edition, Cold Spring Harbor Laboratory press (1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those that confer resistance to drugs, such as G418, hygromycin and methotrexate. Thus, one method of identifying cells having the introduced nucleic acid is by drug selection (e.g., cells that have incorporated the selectable marker gene will survive, while the other cells die). In addition, probing the genome of the cell for the integration of the desired gene or of the marker gene can identify cells having integrated the desired gene.

Clones will also be selected that produce the highest possible recombinant protein yield while maintaining correct post-translational processing. After selection of an optimal clone, the clone is expanded using the RCCS bioreactor as discussed above.

EXAMPLE 5

Transfection of K-562 Cells with Beta-Galactosidase Vector

In initial experiments, a vector containing the reporter gene beta-galactosidase was used to test the efficiency of transfection and express of recombinant protein in K-562 cells grown in the RCCS bioreactor and to establish optimal conditions for expression of the recombinant protein.

The pZeoSV vector containing the beta-galactosidase (Lac Z) reporter gene in the multiple cloning site was obtained from Invitrogen, San Diego, Calif. The pZeoSV plasmid vector also contains a Zeocin resistance gene.

The K-562 cells were transfected with 2 mg of linearized pZeoSVLacZ plasmid, obtained from Invitrogen Corporation, Carlsbad, Calif., in 0.5 ml of Gibco™ Opti-mem media using Gibco™ DMRIE-C transfection reagent (the media and tranfection agent purchased from Invitrogen Corporation, Carlsbad, Calif.) according to the manufacture's instructions. The cells were incubated for 4 hours in this mixture and then 2 ml of complete media, RPMI 1640 with 10% fetal calf serum and 1% penicillin/streptomycin, was added. After 48 hours, the cells were subcultured 1:5 with complete medium plus 100 mg/ml of Zeocin (purchased from Invitrogen Corporation, Carlsbad, Calif.) to select for transfectants. After 19 days of selection, individual transfected cells were cloned and expanded.

The growth rate and integrity of the beta-galactosidase transfected K-562 cells grown in the RCCS was investigated. The cells were placed in the growth chamber of the RCCS-MG with RMPI medium supplemented with 10% heat-inactivated fetal calf serum, 10 mM HEPES (pH 7.2), 40 microgram/ml gentamycin and 2 mM glutamine as previously described for static K-562 cultures. The RCCS-MG was then placed in a humidified incubator with a 5% carbon dioxide and 95% air atmosphere at 37° C. The RCCS-MG chamber was rotated at 10–12 rpm so that the cells remained in suspension and did not have extended contact with the wall or central core of the chamber. The media was changed every 48 hours.

Figure 6:
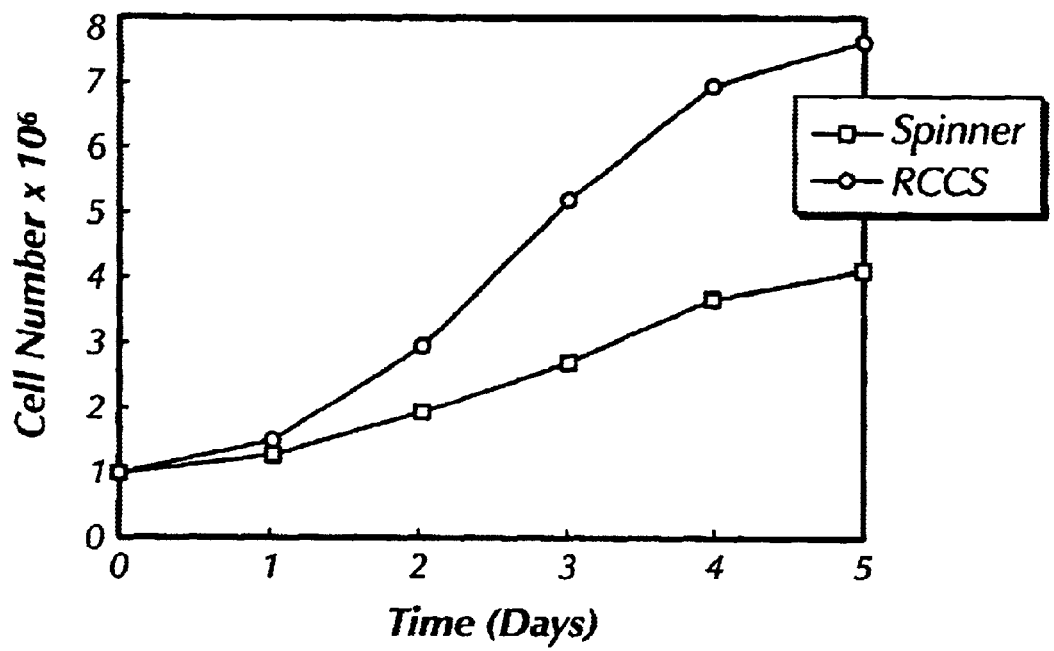
FIG. 6 is a graphical representation of the growth of human myelogenous leukemia cells, K-562, grown in a 50 ml batch rotating cell culture system or a 50 ml spinner flask.

At daily intervals, cell samples were withdrawn from the RCCS-MG and the spinner flask and were counted in a hemocytometer to determine the growth rate of the cells. Cell growth of the K-562 cells seeded and grown in a 50 ml rotating RCCS-MG and a 50 ml spinner flask were compared as shown in FIG. 6. K-562 cells ($1 \times 10^5$ cells/ml) were seeded into the RCCS-MG and the spinner flask. After 5 days, the cells had expanded in the RCCS to $7.4 \times 10^6$ cells/ml, while the cells in the spinner flask had only expanded to $3.8 \times 10^6$ cells/ml. Thus, the cells were almost twice as dense after five days growth in the RCCS-MG as they were in the spinner flask.

Daily cell samples were also monitored for cell viability using trypan blue exclusion. In the RCCS-MG, 95% of the cells were viable by trypan blue exclusion and 78% were viable in the spinner flasks.

Since high growth rates make it difficult to maintain stable media conditions, experiments were performed to determine if changes in media formulation could prolong the life of the culture by reducing the acidity of the media and nutrient utilization. After investigating several media compositions, a specialized media, Stem Pro (a Gibco product made and sold by Invitrogen Corporation, Carlsbad, Calif.), was selected for use. The Stem Pro media reduced the serum requirement in the media from 10% to 2%.

EXAMPLE 6

Transfection of K-562 Cells with PP14 Vector

The cDNA containing the PP14 gene was transfected into K-562 cells using Lipofectamine™ 2000 (Life Technologies). The K-562 cells were used to produce the protein as well as being the source of the mRNA because they have the ability to correctly glycosylate PP14. The transfected cells were resistant to blastocidin and were selected by growing the cells for two weeks in media containing 5 micrograms/ml blastocidin. Individual clones were selected and expanded in culture and then frozen in liquid nitrogen for future use.

Figure 7:
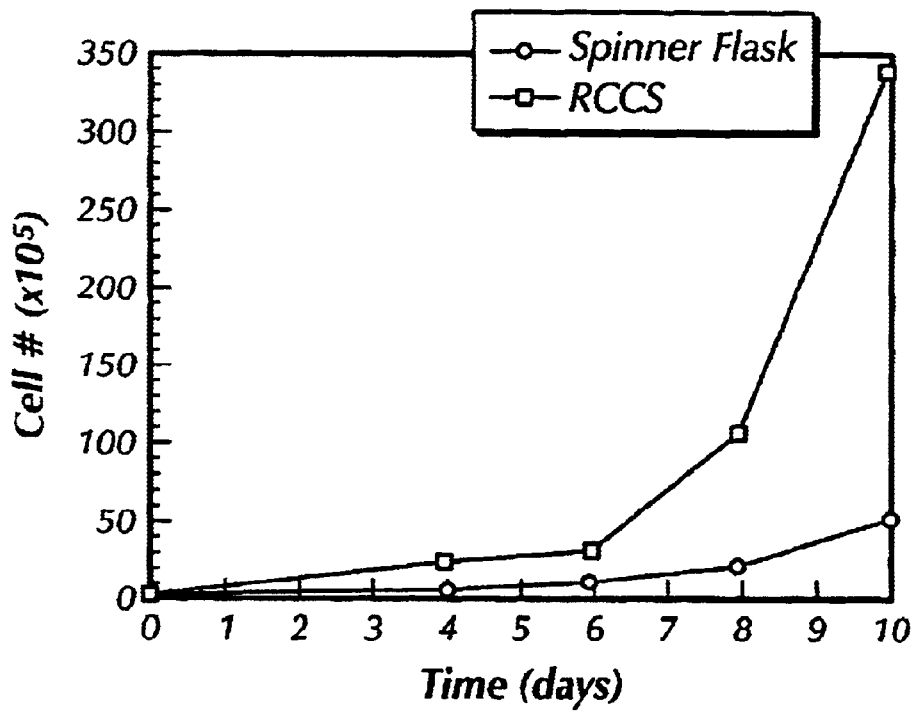
FIG. 7 is a graphical representation of the growth of PP14 transfected human myelogenous leukemia cells, K-562, a perfused rotating cell culture system or a spinner flask.

The growth rates of the PP14 transfected K-562 cells in a spinner flask and a RCCS-MWM culture chamber were compared as shown in FIG. 7. After 10 days in culture, the number of the PP14 transfected K-562 cells in the RCCS- MWM was about seven times the number of the PP14 transfected K-562 cells in the spinner flask.

VI. Production of Recombinant Protein by Human Cells Grown in the RCCS

Recombinant proteins have not been produced in commercial quantities in human cells. The fragility and particularity of human cells have encouraged investigators to use non-human cell lines for producing recombinant proteins. The present invention describes a process for producing recombinant protein in human cells in therapeutic quantities.

EXAMPLE 7

Expression of Recombinant Beta-Galactosidase in Transformed K-562 Cells

A subline of the transfected K-562 cells described above was chosen and seeded in a 50 ml spinner flask and in a 50 ml RCCS bioreactor. After 5 days, the cells were removed from the spinner flask and the RCCS, counted and assayed for beta-galactosidase activity.

The measurement of beta-galactosidase was performed as described in Molecular Cloning: A Laboratory Manual, 2nd Edition, Cold Spring Harbor Laboratory press, 1989. The cells were pelleted by centrifugation at 12,000×g for 10 seconds at room temperature in a microfuge. The pellet was resuspended in 0.25 M TRIS HCl (pH 7.8) and the resuspended cells were disrupted by three cycles of freezing and thawing. The disrupted cells were centrifuged at 12,000×g for 5 minutes at 4° C. in a microfuge.

Figure 8:
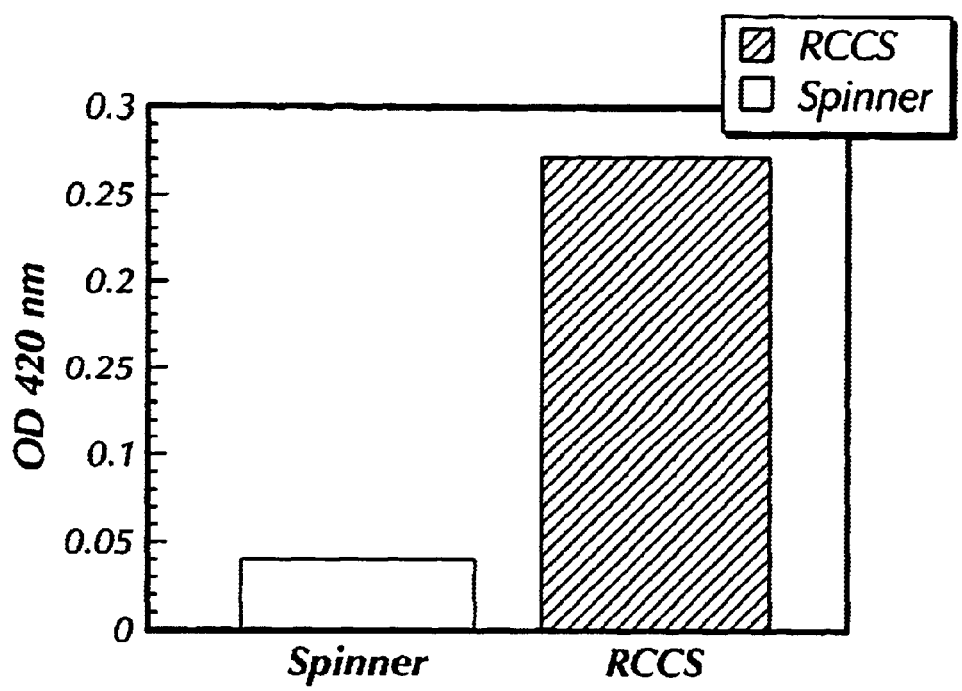
FIG. 8 is a graphical representation of the beta-galactosidase activity, expressed as O.D. 420 nm, of transfected K-562 grown in a 50 ml batch rotating cell culture system or a 50 ml spinner flask.

Each beta-galactosidase assay was run on the lysate of $3 \times 10^6$ transformed cells. The lysate supernatant (5 microliters) was added to 95 microliters of buffer (1 mM $MgCl_2$, 10 mM KCl, and 50 mM 2-mercaptoethanol in 0.1 M Tris, pH 8.0) and mixed with 20 microliters of o-nitrophenyl-beta-D-galactopyranoside (4mg/ml) dissolved in 0.1M sodium phosphate and 0.1 M sodium phosphate (pH 7.5). The mixture was incubated for 2 hours at 37° C. The reaction was then terminated by adding 50 microliters of 1 M sodium carbonate to the mixture. The optical density of the solution was read in a spectrophotometer at 420 nm and the activity of beta-galactosidase was calculated relative to that of cells transfected with the control vector lacking the beta-galactosidase gene. In fact, the cells transfected with the control vector had negligible beta-galactosidase activity while those transfected with the beta-galactosidase had significant activity as shown in FIG. 8.

K-562 cells that had been stably transfected with a beta-galactosidase gene were expanded in a T75 flask and assayed for beta-galactosidase. The cells were then split in equal numbers between an RCCS bioreactor and a spinner flask and grown for 7 days. The cells from each culturing system were harvested and assayed for beta-galactosidase. Since the cells grown in the RCCS had a higher density than cells grown in the spinner flask, the beta-galactosidase activity (O.D. 420 nm) was normalized to cell number as shown in FIG. 8. The cells grown in the spinner flask produced 0.0383 Units LacZ/$10^6$ cells. Whereas the cells grown in the RCCS produced 0.2693 Units LacZ/$10^6$ cells, or approximately a seven fold increase over the cells grown in the spinner flask. It is thought that by relieving cells of the burden of constant injury repair, the bioreactor allows cells to utilize their metabolic energy to perform normal functions such as protein production.

EXAMPLE 8

Bioassay for PP14

Figure 9:
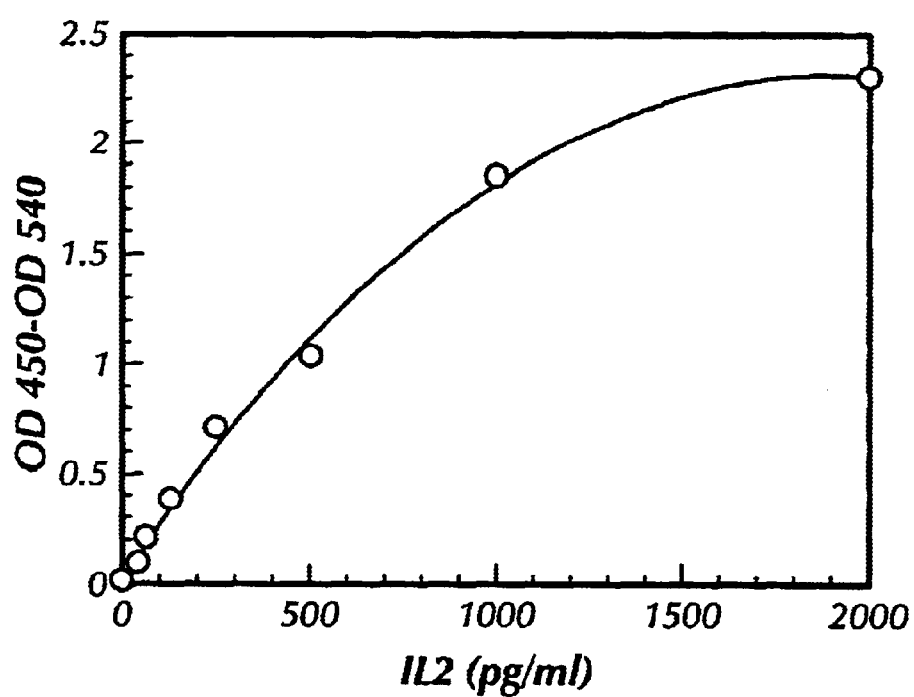
FIG. 9 is a standard curve for IL 2 measured using an ELISA, the results being expressed as O.D. 450–O.D.540.
Figure 10:
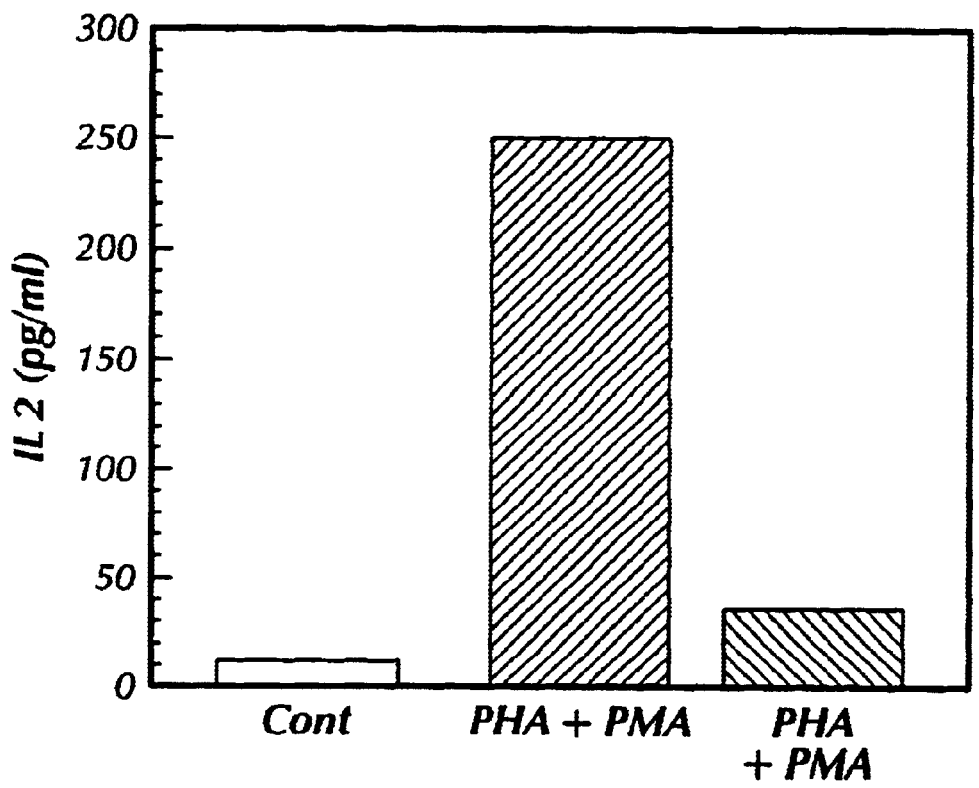
FIG. 10 is a graphical representation of the IL 2 production in control Jurkat cells and Jurkat cells stimulated with phytohemaglutinin and phorbol myristate acetate in the absence and in the presence of PP14.

The bioassay of PP14 is based on the ability of PP14 to inhibit the production of IL2 in Jurkat cells (ATTC# CRL-1990) stimulated by phytohemaglutinin and phorbol myristate acetate (PMA). Jurkat cells were grow in RPMI 1640 with 2 mM 1-glutamine, supplemented with 1 mM pyruvate, 2.5 mM glucose, 10% fetal calf serum and penicillin and streptomycin. The cells were stimulated to produce IL2 by incubation for 24 hours with 1 microgram/ml phytohemaglutinin and 50 nanograms/ml PMA. Jurkat cells were stimulated in the presence or absence of 20 nanograms/ml of PP14. The Jurkat production of IL2 was measured using an ELISA kit from R&D Systems, Minneapolis, Minn. The IL2 standard curve produced with the ELISA is shown in FIG. 9. The Jurkat cells stimulated with the phytohemaglutinin and PMA in the absence of PP14 increased their IL2 production 22 fold; while Jurkat cells stimulated in the presence of 20 ng/ml PP14, produced as described above, inhibited the increase of IL2 by about 90% as shown in FIG. 10.

EXAMPLE 9

Expression of Recombinant PP14 in Transformed K-562 Cells

Single K-562 clones expressing PP14 were seeded into a couple of T25 flasks in RPMI 1640 media containing 10% fetal calf serum, penicillin and streptomycin. After two days of proliferation, the culture was transferred to a 70 ml RCCS-MWM bioreactor or a 50 ml spinner flask. The RCCS-MWM cell culture system was equipped with a 14,000 Dalton molecular weight cut-off membrane so that the PP14 was retained and accumulated within the growth chamber.

Media was changed at 48 hour intervals for each culture system for seven days in the following manner. The entire contents of the spinner flask were removed with each media change, the cells pelleted by centrifugation, resuspended in fresh media and placed back into the spinner flask. For the cells grown in the RCCS-MWM culture system, the media feed bottle containing 200 ml of media was replenished with fresh media every 48 hours. At the same time a 10 ml sample of media was withdrawn from the cell chamber, the cells pelleted by centrifugation, resuspended in fresh media and returned to the growth chamber of the RCCS-MWM. At various times between media changes, the pH of the media was measured and readjusted to approximately 7.4 with NaOH. The supernatants from all the 10 ml samples were frozen for later purification. At the end of the culture period, cell counts were made in each culture system.

Figure 11:
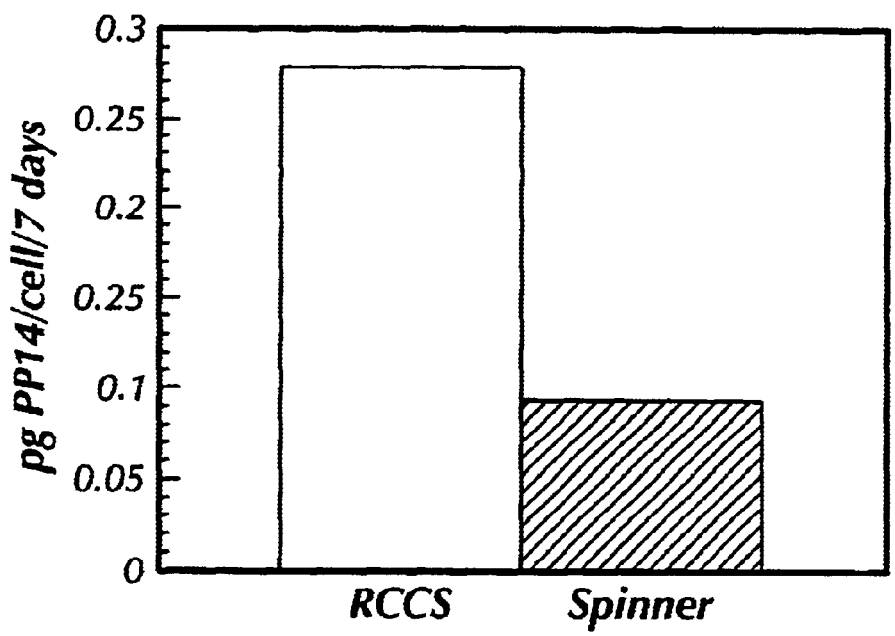
FIG. 11 is a graphical representation of the production of PP14 by K-562 cells, transfected with PP14 DNA, grown in a rotating cell culture system or a spinner flask.

PP14 was processed by pooling the media collected at each interval, filtering the pooled media through a 0.45 micron filter and dialyzing it against 20 mM $Na_2HPO_4$, pH 7.1. The dialysate was applied to a Cibacron Blue F3GA column (Econo-Pac Blue Cartridge, Bio-Rad, Hercules, Calif.) and eluted with the same buffer. The Cibacron Blue F3GA column is designed to specifically bind albumin. Thus, most of the albumin in the media was retained on the column allowing PP14 and other proteins to pass though. The eluate was applied to a metal affinity chelate column (HiTrap Chelating HP, Amersham Biosciences, Piscataway, N.J.) to bind the PP14 that was engineered with a polyhistidine tag. NaCl was added to the eluate to a concentration of 0.5 M before it was loaded onto the column. The column was washed with 10 column volumes of binding buffer (i.e., 20 mM $Na_2HPO_4$/0.5 M NaCl, pH 7.1) and eluted with binding buffer plus 500 mM imidazole. The fraction containing protein ($A_{280}$) was collected and dialyzed against phosphate buffered saline, pH 7.4. The total protein in the metal chelate eluate (i.e., PP14) was measured by the method of Bradford (Anal. Biochem. 72:248, 1976). The production of PP14 in each culture system was expressed per cell per week using cell counts made at the end of the bioreactor run. FIG. 11 illustrates the amount of PP14 produced per cell over a seven day period by cells grown in the RCCS-MWM culture system and by the cells grown in the spinner flask. The cells grown in the RCCS-MWM culture system produced 2.98 times the amount of PP14 produced by the cells grown in the spinner flask.

Figure 12:
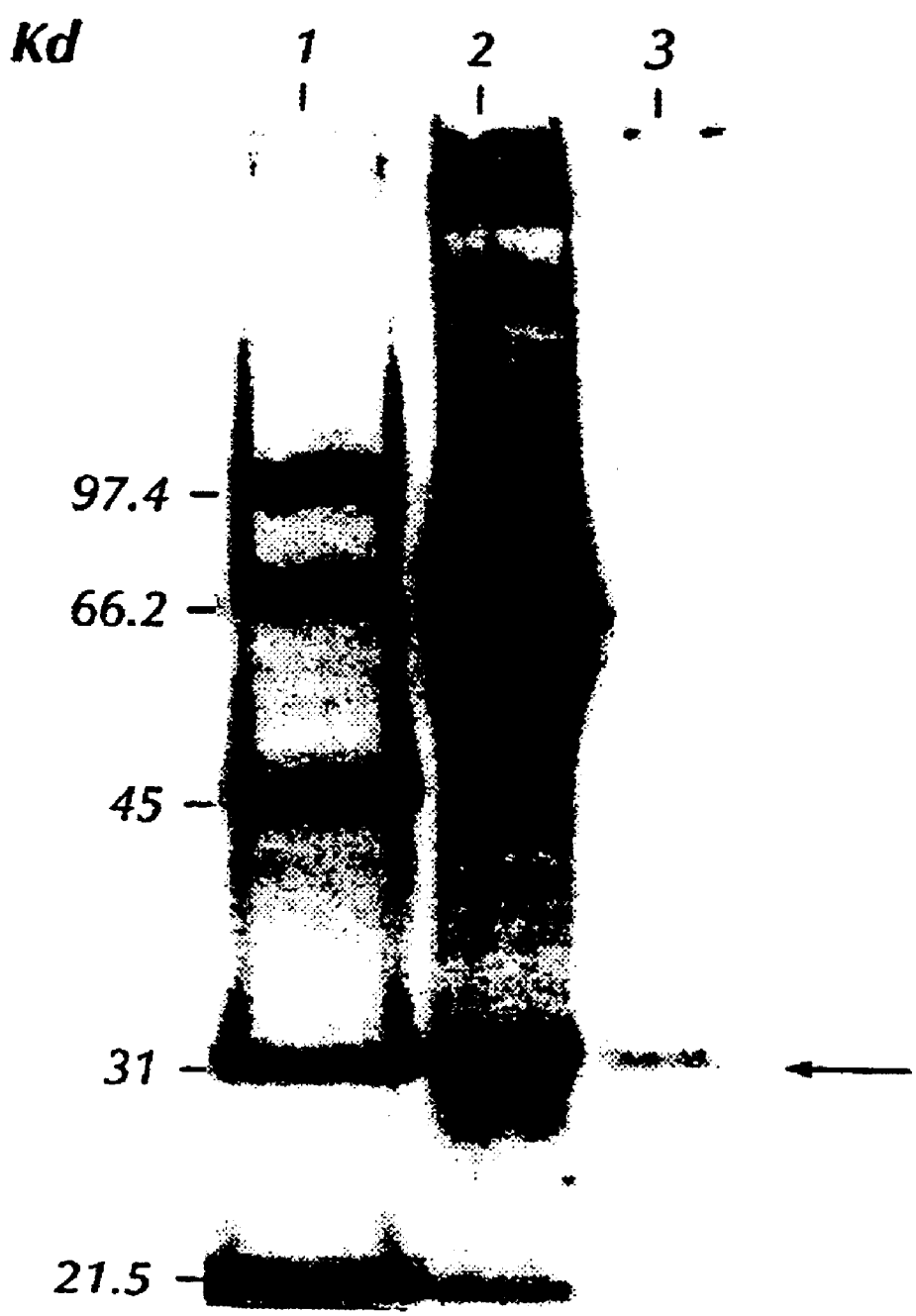
FIG. 12 is a photograph of an SDS PAGE gel showing molecular weight standards (Lane 1), the total protein in the culture media in which the PP14 transfected K-562 cells were grown (Lane 2), and purified PP14 (Lane 3)

A sample of the eluted protein fraction was electrophoresed on a 10% SDS PAGE gel and stained with GelCode Blue Stain Reagent (Pierce, Rockford, Ill.). FIG. 12 is a photograph of the SDS PAGE gel where Lane 1 shows molecular weight standards (i.e., phosphorylase b at 97,400 Daltons, serum albumin at 66,200 Daltons, ovaalbumin at 45,000 Daltons, carbonic anhydrase at 31,000 Daltons, and trypsin inhibitor at 21,500 Daltons); Lane 2 shows the total protein in the culture media in which the PP14 transfected K-562 cells were grown, and Lane 3 shows the protein eluted from the affinity column as a 28 kDaltons band (i.e., the molecular weight of PP 14).

EXAMPLE 10

Expression of Recombinant PP14 in Transformed K-562 and Chinese Hamster Ovary Cells Chinese Hamster Ovary cells were also transfected with PP14 using the same procedure as described above for the K-562 cells. The PP14 transfected K-562 and CHO cells were cultured in the RCCS-MWM culture system and the PP14 produced by each cell line was purified and quantified.

Figure 13:
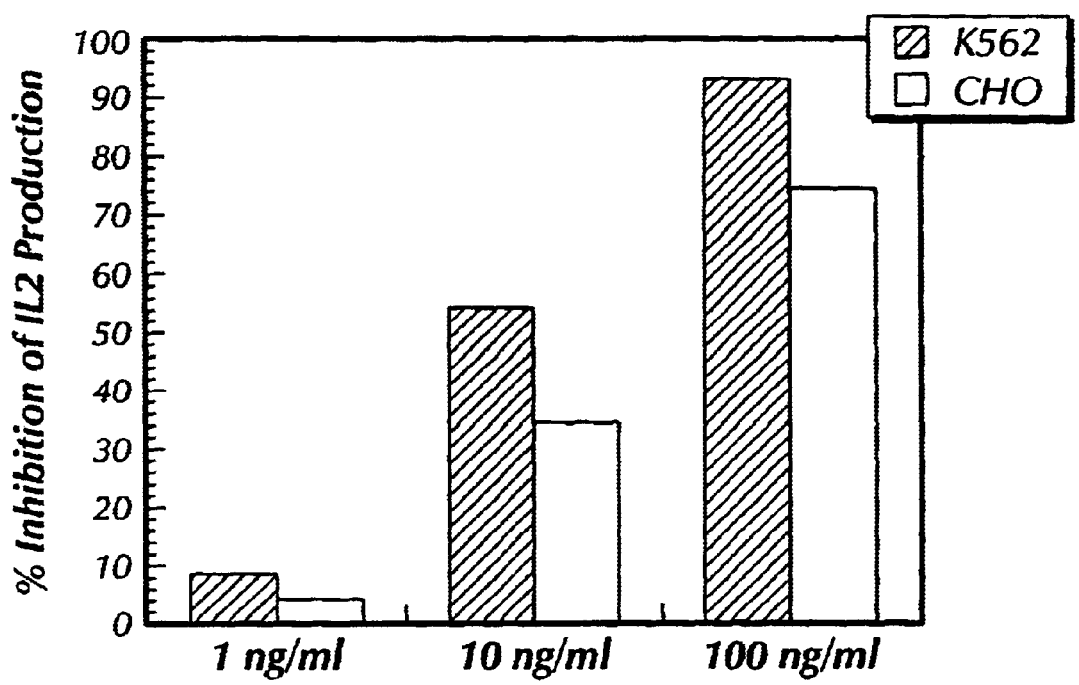
FIG. 13 is a graphical representation of the effective inhibitory activity of 1 ng/ml, 10 ng/ml, and 100 ng/ml PP14 of PP14 produced by PP14 transfected CHO cells and K565 cells grown under similar conditions in a rotating cell culture system.

The activity of the purified PP14 was measured using the bioassay described above. FIG. 13 shows the effective inhibitory activity of 1 ng/ml, 10 ng/ml and 100 ng/ml PP14 produced by PP14 transfected CHO cells and K-562 cells grown under similar conditions in the RCCS-MWM culture system. The specific activity of the PP14 produced by the human K-562 cells was consistently higher than the specific activity of the PP14 produced by the CHO cells.

CONCLUSION

The present invention produces recombinant protein using a unique process. Higher expression rates, greater yields, and increased specific activity of therapeutic proteins can be realized with this new production system. This invention can be used for commercial protein production, thereby resulting in, for example, new biotherapies to treat disease and more sensitive diagnostic agents to detect life-threatening illness sooner.

Any protein that requires complex post-translational processing can be advantageously produced by the method of the present invention, where the protein can be the result of expression of any gene of interest. The method of the present invention therefore provides for production of post-translationally modified recombinant human proteins that are produced in high concentrations relative to other conventional methods and produces proteins that are closer in structure to native proteins than proteins produced by other conventional methods. In the context of the present invention, "high yield" or "high concentration" means that the recombinant protein is produced in quantities that are greater than the quantities produced by other conventional methods, resulting in efficient production that is less expensive.

Although the present invention and its advantages have been described in detail, it should be understood that various changes, substitutions, and alterations can be made to the combination drug product of the present invention without departing from the spirit and scope of the invention as defined by the appended claims.

REFERENCES

All patents and publications mentioned in this specification are indicative of the level of skill of those of knowledge in the art to which the invention pertains. All patents and publications referred to in this application are incorporated herein by reference to the same extent as if each was specifically indicated as being incorporated by reference and to the extent that they provide materials and methods not specifically shown.

Anderson, et al., U.S. Pat. No. 6,080,581 issued Jun. 27, 2000.

Bolton, A. E., Clough, K. J., Stoker, R. J., Pockley, A. G., Mowles, E. A., Westwood, O. M. R., and Chapman, M. G. Identification of placenta protein 14 as an immunosupressive factor in human reproduction. Lancet 1:593–595, 1987

Carbohydrates and Glycobiology: Searching for Medicine's Sweet Spot in Science 291:2338, 2001

Cherry, R. and Papoutsakis, E. T., Physical Mechanisms of Cell Damage in Microcarrier Cell Culture Bioreactors. Biotechnolo. Bioeng. 32:1001–1014, 1988.

Cherry, R. S. and Hulte, C. T., Cell Death in the Thin Films of Bursting Bubbles. Biotechnol. Prog. 8:11–18, 1992.

Croughan, M. and Wang, D. I. C., Growth and death in overagitated microcarrier cell cultures. Biotechnol. Bioeng. 33: 731–744, 1989.

Curling, E. M., Hayter, P. M., Baines, A. J., Bull, A. J., Gull, K., Strange, P. G., and Jenkins, N. Recombinant human interferon-γ. Differences in glycosylation and proteolytic processing lead to heterogeneity in batch culture. Biochem. J. 272: 333–337, 1990.

Furmanski, P., A pregnant possibility: Crossing fetal tolerance with hematopoiesis. Am. J. Pathol. 145: 1485–1495, 1994.

Goodwin, T. J., Prewitt, T. L., Wolf, D. A. and Spaulding, G. F., Reduced Shear Stress: A Major Component in the Ability of Mammalian Tissues to Form Three Dimensional Assemblies in Simulates Microgravity. J. Cell Biochem. 51:310–311, 1993.

James, D. C., Freedman, R. B., Hoare, M., Ogonah, O. W., Rooney, B. C., Larionov, O. A., Dobrovolsky, V. N., Lagatin, O. V., Jenkins, N. N-Glycosylation of Recombinant Human Interferon-γ Produced in Different Animal Expression Systems. Biotechnology 13:592–596, 1995.

Julkunen, M., Seppälä, M. and Jänne, O. A. Complete amino acid sequence of human placental protein 14: A progesterone-regulated uterine homologous to β-lactoglobulins. Proc. Natl. Acad. Sci. USA 85: 8845–8849, 1988.

Julkunen, M., Wahlstrom, T., Seppala, M., Koistinen, R., Koskimies, A., Stenmar, U. H. and Bohn, H., Detection and Localization of Placental Protein 14-Like Protein in Human Seminal Plasma and in the Male Genital Tract. Arch Androl. 12 (Suppl):59–67,1984.

Kunas, K. T. and Papoutsakis, E. T., Damage mechanisms of suspended animal cells in agitated bioreactors with and without bubble entrainment. Biotechnol. Bioeng. 36:476–483, 1990.

Molecular Cloning: A Laboratory Manual, 2nd Edition, Cold Spring Harbor Laboratory press, 1989.

O'Connor et al., U.S. Pat. No. 5,962,324 issued Oct. 5, 1999.

Okamoto, N., Uchida, A., Kenji, T., Yoshitaka, K., Hideharu, K., Rittinen, L., Koistinen, R., Seppälä, M., Mori, T. Suppression by human placental protein 14 of natural killer cell activity. Am. J. Reprod. Immunol. 26: 137–142, 1991.

Park, J. H., Lee, J. M. and Park, I. S., Production of Recombinant Endostatin from Stably Transformed Drasophila Melanogaster S2 Cells. Biotechnology Lett. 21:729–733, 1999.

Petersen, J. F., McIntire, L. V., and Papoutsakis, E. T., Shear sensitivity of cultured hybridoma cells (CRL-8018) depends on mode of growth, culture age and metabolite concentration. J. Biotechnol. 7: 229, 1988.

Pockley, A. G. and Bolton, A. E. Placental protein 14 (PP14) inhibits the synthesis of interleukins-2 and the release of soluble interleukins 2 receptors from phytohemaglutinin-stimulated lymphocytes. Clin. Exp. Immunol. 77: 252–256, 1989.

Pockley, A. G. and Bolton, A. E., The Effect of Human Placenta Protein 14 (PP14) on the Production of Interleukin 2 from Mitogenically Stimulated Mononuclear Cell Cultures. Immun. 69:277–281, 1990.

Pockley, A. G., Mowles, E. A., Stoker, R. J., Westwood, O. M. R., Chapman, M. G., and Bolton, A. E. Suppression of in vitro lymphocyte reactivity to phytohemaglutinin by placental protein 14. J. Reprod. Immunol. 13: 31–39, 1988.

Proceedings of the 13$^{th}$ Annual Meeting of the IUPS Commission on Gravitational Physiology. San Antonio, Physiologist 35 (1 Suppl.): S49–S58, 1992.

Spaulding, et al., U.S. Pat. No. 5,637,477 issued Jun. 10, 1997.

Schwartz, et al., U.S. Pat. No. 5,026,650 issued Jun. 25, 1991.

Unsworth, B. R. and Lelkes, P. I., Growing tissues in microgravity. Nature Medicine 4(8): 901–907, 1998.

What is claimed is:

1. A method for production of a human proteinaceous therapeutic molecule comprising:
   (a) identifying a mammalian cell line derived from a tissue that produces the proteinaceous therapeutic molecule in nature;
   (b) transfecting a plurality of cells from the mammalian cell line with a gene coding for the human proteinaceous therapeutic molecule;
   (c) cloning the transfected cells expressing the human proteinaceous therapeutic molecule;
   (d) expanding the cloned cells in a rotating cell culture system filled with a culture medium, wherein the rotating cell culture system provides a simulated microgravity environment for the expanding cloned cells and a membrane carrier assembly transverses a growth compartment, the membrane carrier comprising a support cylinder having a first end in communication with a fluid inlet and a second end in communication with a fluid outlet, a molecular weight cut-off membrane secured to an exterior surface of the support cylinder, and a medium circulation chamber between the exterior surface of the cylinder and an interior surface of the membrane, the chamber in fluid communication with the fluid inlet and the fluid outlet;
   (e) growing the cloned transfected cells in the rotating cell culture system, wherein the cloned cells synthesize the human protein and secrete the human protein into the culture medium in the rotating cell culture system:
   (f) separating a volume of culture medium from the expanded cloned cells; and
   (g) isolating a protein fraction from the volume of culture medium, wherein the protein fraction is rich in the proteinaceous therapeutic molecule.

2. The method of claim 1, wherein the human proteinaceous therapeutic molecule is post-translationally modified.

3. The method of claim 1, wherein the human proteinaceous therapeutic molecule is PP14.

---

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence:PCR Primer

<400> SEQUENCE: 1
agggagcagc ctcccctggc aat                                    23

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence:PCR Primer

<400> SEQUENCE: 2
catccctctg gctccagagc tcaga                                  25

4. The method of claim 1, wherein the mammalian cell line is a human derived cell line.

5. The method of claim 3, wherein the mammalian cell line is a human myelomous leukemia cell line.

6. The method of claim 1, wherein the gene coding for the human proteinaceous therapeutic molecule includes a bioselection mechanism.

7. The method of claim 6, wherein the bioselection mechanism is a Blasticidin S HCl resistance.

8. The method of claim 1, wherein the gene coding for the human proteinaceous therapeutic molecule includes a polyhistidine fusion tag.

9. The method of claim 1, wherein the rotating cell culture system provides a low-shear environment equal to 2 dynes/cm$^2$ or less.

10. The method of claim 1, wherein the rotating cell culture system rotates from about 10 rpm to about 20 rpm.

11. The method of claim 1, wherein the molecular weight cut-off membrane has a molecular weight cut-off value that is greater than the molecular weight of the human proteinaceous therapeutic molecule.

12. The method of claim 1, further comprising the step of providing a continuous flow of the culture media to the cloned cells in the rotating cell culture system.

13. The method of claim 12, wherein the continuous flow of culture media is oxygenated through an external gas exchange membrane.

14. The method of claim 1, wherein the protein fraction is isolated using a column material designed to remove serum albumin from the culture medium.

15. The method of claim 8, wherein the protein fraction is isolated using a metal chelate column.

16. A method for the production of recombinant human proteins comprising:
   (a) selecting a post-translationally modified human protein;
   (b) identifying a human cell line derived from a tissue that produces the human protein;
   (c) transfecting a plurality of cells from the human cell line with a gene coding for the human protein and a gene coding for a bioselection mechanism;
   (d) cloning the transfected cells expressing the human protein and the bioselection mechanism;
   (e) introducing the cloned transfected cells into a rotating cell culture system filled with a culture medium, wherein the rotating cell culture system has a membrane carrier assembly transversing a growth compartment, the membrane carrier comprising a support cylinder having a first end in communication with a fluid inlet and a second end in communication with a fluid outlet, a molecular weight cut-off membrane secured to an exterior surface of the support cylinder, and a medium circulation chamber between the exterior surface of the cylinder and an interior surface of the membrane, the chamber in fluid communication with the fluid inlet and the fluid outlet; and
   (f) growing the cloned transfected cells in the rotating cell culture system, wherein the cloned cells synthesize the human protein and secrete the human protein into the culture medium in the rotating cell culture system.

17. The method of claim 16, wherein the human protein is PP14.

18. The method of claim 16, wherein the human cell line is human myelomous leukemia cell line.

19. The method of claim 16, wherein the bioselection mechanism is an antibiotic resistance.

20. A method for the production of recombinant human proteins comprising:
   (a) selecting a post-translationally modified human protein;
   (b) identifying a human cell line derived from a tissue that produces the human protein;
   (c) transfecting a plurality of cells from the human cell line with a gene coding for the human protein and a bioselection mechanism;
   (d) cloning the transfected cells expressing the human protein and the bioselection mechanism;
   (e) providing a culture chamber comprising
      (i) a tubular housing;
      (ii) a growth compartment within the housing;
      (iii) a fluid inlet;
      (iv) a fluid outlet; and
      (v) a membrane carrier assembly transversing the growth compartment including a support cylinder having a first end in communication with the fluid inlet and a second end in communication with the fluid outlet, a molecular weight cut-off membrane secured to an exterior surface of the support cylinder, and a medium circulation chamber between the exterior surface of the cylinder and an interior surface of the membrane, the chamber in fluid communication with the fluid inlet and the fluid outlet;
   (f) introducing the cloned transfected cells into the growth chamber of the rotating cell culture system filled with a culture media;
   (g) maintaining a flow of the culture media through the growth chamber of the rotating cell culture system;
   (h) expanding the cloned transfected cells in the rotating cell culture system, wherein the cloned cells synthesize the human protein and secrete the human protein into the culture medium in the rotating cell culture system;
   (i) separating the cloned transfected cells from a volume of the culture medium containing the secreted human protein; and
   (j) isolating a protein fraction from the volume of the culture medium, wherein the protein fraction is rich in the human protein.

21. The method of claim 20, wherein the molecular weight cut-off membrane has a molecular weight cut-off value that is less than a molecular weight of the human protein.

22. The method of claim 21, wherein the human protein accumulates in the growth chamber of the rotating cell culture system.

23. The method of claim 20, wherein the protein fraction is isolated using a column material designed to bind and remove albumin from the volume of culture medium without binding and removing the human protein from the volume of culture media.

* * * * *